(12) United States Patent
Garland

(10) Patent No.: US 7,192,277 B2
(45) Date of Patent: *Mar. 20, 2007

(54) DENTAL MODEL TRAY USED IN FORMING DENTAL MODEL

(76) Inventor: James K. Garland, 3255 E. Seven Springs Dr., Sandy, UT (US) 84092

( * ) Notice: Subject to any disclaimer, the term of this patent is extended or adjusted under 35 U.S.C. 154(b) by 0 days.

This patent is subject to a terminal disclaimer.

(21) Appl. No.: 11/124,336

(22) Filed: May 9, 2005

(65) Prior Publication Data

US 2005/0191595 A1  Sep. 1, 2005

Related U.S. Application Data

(63) Continuation of application No. 10/204,531, filed as application No. PCT/US01/05683 on Feb. 21, 2001, now Pat. No. 6,910,888.

(60) Provisional application No. 60/184,838, filed on Feb. 24, 2000.

(51) Int. Cl.
*A61C 9/00* (2006.01)

(52) U.S. Cl. .......................................... 433/34

(58) Field of Classification Search .................. 433/34, 433/37, 45, 60
See application file for complete search history.

(56) References Cited

U.S. PATENT DOCUMENTS

| 4,265,619 | A | * | 5/1981 | Lucki et al. .................. 433/54 |
| 5,775,899 | A | * | 7/1998 | Huffman ....................... 433/60 |
| 6,106,284 | A | * | 8/2000 | Cronin et al. ................. 433/34 |

* cited by examiner

*Primary Examiner*—Melba Bumgarner
(74) *Attorney, Agent, or Firm*—Terry M. Crellin

(57) ABSTRACT

Tray (10) for forming dental model comprises base wall (12) forming floor upon which dental casting material is poured. Spaced apart projections (14) extending upwardly from base wall (12). An upstanding axis of each projection (14) is substantially perpendicular to the upper face of the base wall (12). Projections (14) are arranged in two rows, with the projections (14) in one row being offset from corresponding projections (14) in the other row. Sidewalls of each projection (14) taper inwardly at an angle of between about 82 to 88 degrees with the upper face of the base wall (12). Each projection (14) has a thickness at its base of about 3 to 7 millimeters. The projections (14) are spaced from each other at their bases by a distance of from 0 to 5 millimeters.

4 Claims, 1 Drawing Sheet

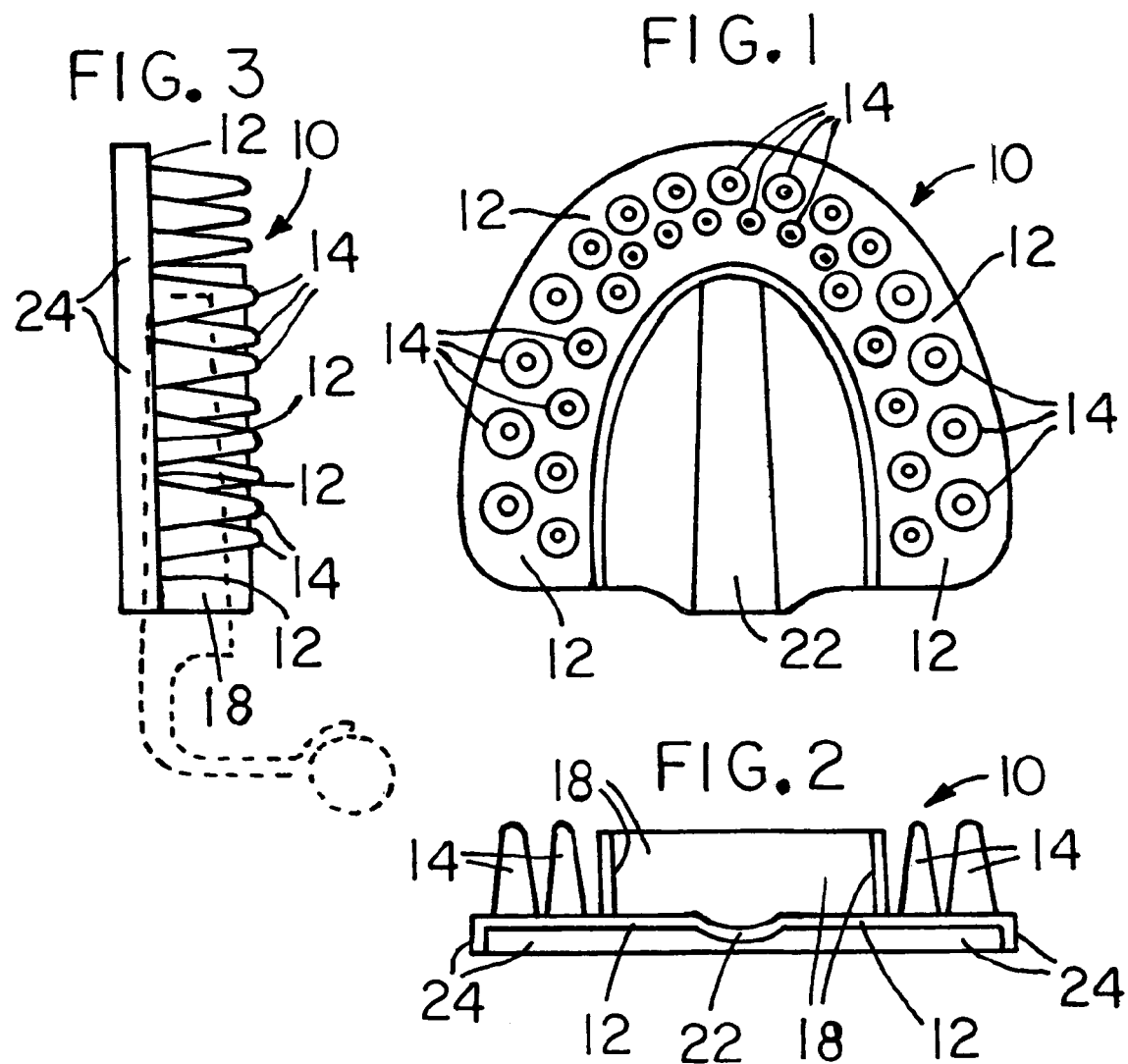

DENTAL MODEL TRAY USED IN FORMING DENTAL MODEL

BACKGROUND OF THE INVENTION

1. Field of the Invention

The present invention relates to trays used by laboratory technicians in making a dental model from casting material that is poured on the tray.

2. State of the Art

Dental trays have been used in the prior art wherein casting material is poured on the tray and a dental model is then formed in the casting material. A system in the prior art utilized a plurality of metal pins that extended upwardly from the upper surface of the tray, with the casting material being poured over the pins. The resulting dental model could then be cut so as to isolate one or more dies corresponding to teeth upon which a crown or other prosthetic device was to be formed. The die or dies could then be placed back on the tray, and the correspondence of the pins extending from the tray into the die or dies would result in proper positioning of the die or dies relative to the dental model.

A problem with the tray having metal pins is that the metal pins must be formed by precision machining and thus the trays are relatively very expensive. Dental labs are very reluctant to use the trays because of their exorbitant cost. It would be highly desirable to produce an inexpensive tray that did not use the expensive machined metal pins, such as a tray made of polymeric material in which the pins are formed integrally with the tray from the same polymeric material. Unfortunately, if one makes a tray of polymeric material having pins made of the same polymeric material, with the pins being spaced apart and shaped similar to the metal pins of the prior art trays, the tray with pins made of polymeric material is totally useless. The tray has shortcomings that prevent it from being a viable tool to be used in making a satisfactory dental model.

The metal pins of the prior art dental tray are sufficiently rigid to retain dies that have been cut from a dental model that has been cast in place on the dental tray. However, with pins made of polymeric material and having a similar size and shape as the metal pins of the trays of the prior art, the resulting pins made of polymeric material are too flexible and do not have sufficient rigidity. A dental model can be cast on such pins, but when the dental model is cut into dies, and the dies are replaced on their mutually respective pins, the individual dies are not stable, i.e., the pins flex and allow the dies to move to and away from adjacent dies or adjacent portions of the model. This is because the pins made of polymeric material are not sufficiently rigid, they flex and thus allow do not hold the dies firmly in their proper orientation. Cutting of the dies from the model results in a portion of the die equal to the thickness of the saw being removed from the die. When the die is replaced in the model there is a space equivalent to the thickness of the saw on each side of the die. When the pins are not sufficiently rigid to prevent the die from moving back and forth within that space formed by the saw cuts, then the die cannot be used in forming a precision prosthetic thereon, and the resulting dental model is not useful.

OBJECTIVES AND BRIEF DESCRIPTION OF THE INVENTION

A principal objective of the invention is to provide a dental model tray that is made of a polymeric material and which has upstanding projections that are formed integrally with the tray from the same polymeric material as the tray.

A further objective of the present invention is to provide such a dental model tray wherein a plurality of spaced, apart, elongate projections extend upwardly from an upper face of the base wall of the dental model tray, with the projections being arranged in first and second, substantially parallel row, with the first row being offset from corresponding projections in the second row.

A still further objective of the present invention is to provide such a dental model tray in which each of the projections have upstanding sidewalls that taper inwardly from their attachment to the base wall toward a central, upright axis of each of said projections so that the sidewall of each of the projections makes an angle of between about 82 degrees and 88 degrees with the upper face of the base wall of the dental model.

The above objectives are achieved in accordance with the present invention by providing a novel dental model tray formed of a polymeric material that has a plurality of upstanding projections formed integrally therewith, wherein the projections extend into a cast dental model formed on the tray to hold the dental model, including dies of individual teeth that have been cut from the dental model, firmly to the dental model tray. It was not obvious that such a dental model tray could be formed of polymeric material, and in fact it appeared to be an insurmountable task, as will be now explained.

The dental model that is cast on the tray, including individual dies that are cut from the formed dental model, are held in relocation position on the dental model by the upstanding projections. This retention comes solely from the engagement of the cast dental model and any dies cut from the dental model with the upstanding projections of the dental model tray that extend into the interior of the dental model and dies that are cut from the dental model. The problem, which appeared to be insurmountable, is to form such a dental tray from polymeric material.

Polymeric material and the casting material from which a dental model are made have opposing thermal expansion and when the casting material sets, it has a markedly different expansion qualities as compared to the polymeric material. These differences make it appear that the plastic materials and the casting material are incompatible with each other. When trays made of polymeric material are used which have upstanding sidewalls that form a channel into which the casting material is poured, the polymeric material of the sidewalls expands as it is heated by the heat generated as the casting material sets. Eventually, the set casting material cools, and the sidewalls of the tray made of polymeric material also cools. The sidewalls shrink as the polymeric material cools, and to make matters worse, the set casting material expands during the setting and cooling of the material. This results in the set casting material being so tightly held within the sidewalls of the tray that the casting material is hard to remove and relocate. It especially becomes difficult to remove and relocate dies that are cut from the casting with any accuracy.

It has been unexpectedly found that when a double row of projections extend from the base or floor of the tray, with the tray and the projections being formed integrally of the same polymeric material and the projections have particular structural characteristics in accordance with the present invention as will be more fully described hereinafter, the double row of projections form and ideal retention mechanism for the cast dental model to be retained on the tray. One unexpected result is that any dies cut from the dental model can be repositioned on the tray in their precise, correct position relative to the rest of the dental model. The projections made of polymeric material and in accordance with the particular structural characteristics in accordance with this invention are inflexible ad do not allow the dies to move, but instead firmly hold the dies in their proper, stable position. In addition, the problem with the differences in heating and expansion characteristics of the polymeric material and the casting material can be utilized as a benefit when the particular structural parameters of the present invention are maintained in the creation of the dental tray that is made of polymeric material.

When casting material is poured around the projections, the heat produced by the setting of the casting material heats the polymeric material of the projections, and the projections expand. Then, as the set casting material cools, the projections shrink. However, when the particular structural characteristics of the present invention are maintained in the projections, it has been found that the expansion of the casting material during the setting and cooling can be used to offset the shrinkage of the polymeric material from which the projections are made. When the structural characteristics of the present invention are maintained, it has been found that the resulting dental model that is cast around the projections can be readily removed and replaced on the tray without sticking tightly to the projections. Further, it has also been quite unexpectedly found, that the cast dental model, and especially any dies that are cut from the model, will be held sufficiently on the tray by the projections to prevent the dental model and die or dies from falling from the tray as the tray is being used in forming the prosthetic device for one or more of the teeth of the dental model. The dies can be removed from the dental model and replaced, with the dies being relocated with exceptional accuracy relative to the remaining dental model.

Utilizing a tray made of polymeric material having integral projections extending therefrom and made, of course, from the same polymeric material has been found to be possible when the structural parameters of the present invention are maintained, as will be discussed in detail hereinafter. The unexpected goal achieved by the present invention is to provide a dental model tray made of polymeric material which is capable of retaining removable dies with ease of removal of the dies from the model, with accuracy of relocation of the dies, and with retention of the dies and the model on the tray during processing of the prosthetic device which is to be made. If the structural parameters are not maintained stability of the dental model and the removable dies is not adequate.

Additional objects and features of the invention will become apparent from the following detailed description, taken together with the accompanying drawings.

THE DRAWINGS

A preferred embodiment of the present invention representing the best mode presently contemplated of carrying out the invention is illustrated in the accompanying drawings in which:

FIG. 1 is a top plan view of one preferred embodiment of a dental model tray of the present invention;

FIG. 2 is a back elevation of the dental model of FIG. 1; and

FIG. 3 is a left side elevation of the dental model of FIG. 1.

DETAILED DESCRIPTION OF THE ILLUSTRATED EMBODIMENTS

Referring now to FIGS. 1–3, a dental model tray 10 is shown. The tray 10 has a substantially planar base wall 12 upon which dental casting material (not shown in drawings) is poured informing a dental model. The base wall 12 if formed from a polymeric material and a plurality of spaced apart, elongate projections 14 are formed integrally with the base wall 12. The projections 14 extend upwardly from an upper face of the base wall 12 so that an elongate axis of each of the projections 14 is substantially perpendicular to the upper face of the base wall 12. The projections are advantageously molded integrally with the base wall 12 and are thus formed of the same polymeric material as the base wall 12.

The projections 14 are arranged in first and second rows that are substantially parallel with each other. The projections 14 in the first row are offset from corresponding projections 14 in the second row so that any two adjacent projections 14 in one row and an adjacent, corresponding projection in the other row are spaced from each other in a triangular configuration. Each of the projections 14 have upstanding sidewalls that taper inwardly from their attachment to the base wall 12 toward a central, upright axis of each of the projections 14 so that the sidewall of each of the projections 14 makes an angle of between 82 to 88 degrees with the upper face of the base wall 12.

As has been shown by extensive experiments, the angle of the taper of the sidewalls of the projections 14 is critical. The angle must fall within the range as given above. In a preferred embodiment of the present invention, the taper of the projections 14 is such that the sidewalls of the projections 14 make an angle of between about 83 degrees and 87 degrees with the upper face of the base wall 12. In a most preferred embodiment of the invention, the sidewalls of the projections 14 make an angle of about 85 degrees with the upper surface of the base wall 12.

The projections 14 can have any desired cross-sectional shape, however a curvilinear shape such as circular (as shown in the drawings) or ovular is preferred. If the cross-sectional shape of the projections 14 is triangular or the shape of other polygons, then the edges of the longitudinal edges formed on the sidewalls of the projections 14 by the cross-sectional shape of the sidewalls must be rounded so that the surface of each of the projections 14 is smooth and has no sharp edges. The top of each projection 14 should be rounded so that there is no sharp point.

The projections 14 should have a cross-sectional dimension at their bases, i.e., at their point of connection to the base wall 12, of between about 3 millimeters and 7 millimeters. The projections 14 can be spaced so that the bases of the projections 14, i.e., their point of connection to the base wall 12, touch each other or are spaced from the bases of any adjacent projection by a distance up to about 5 millimeters. In other words, the spacing between the bases of the projections 14 can be between 0 millimeter and about 5 millimeters.

The height or length of the projections 14 from the upper face of the base wall 12 should be at least 6 to 7 millimeters, and more preferably at least about 7 to 12 millimeters. Most preferably, the height of the projections 14 should be between about 8 millimeters and 10 millimeters. Expressed another way, the height or length of the projections 14 measured as a ratio of that height or length with respect to the height of the die that is to be made using the dental tray should be between about ⅓ to ⅔.

A retention control wall 18 can be provided if so desired. The control wall 18, if present, is formed integrally with the base wall 12 of the tray 10, with the retention wall 18 being located alongside either of the two rows of projections 14. As illustrated in the drawings, the retention wall 18 is located adjacent to the inner row of projections 14. The retention wall 18 is preferably spaced from the adjacent row of projections by a distance of between about 1 millimeter and 6 millimeters. The height of the retention wall 18 will generally be about the same as the height of the projections 14 or up to 1 or 2 millimeters less than the height of the projections 14.

Means for attaching an articulation device is provided. Because various articulation devices are available in the art, various different means of attaching the articulation device to the tray of the present invention are possible, and there will be no attempt here to identify and describe all such articulation devices and means of attachment to the tray. A very useful articulation device is shown in my U.S. Pat. No. 5,846,076, issued on Dec. 8, 1998, and as shown in the drawings, the leg of the articulation device which is shown in dotted lines in FIGS. 2 and 3 is positioned along a guide built into the tray. Casting material is then poured around the leg of the articulation device to hold it firmly in place. As shown in the drawings, a cradle 22 is formed in the upper face of the base wall 12, and the leg of the articulation device is positioned in and along the guide 22. Casting material is then poured on the tray 10 so as to encapsulate the distal end portion of the leg of the articulation device and hold it firmly attached to the tray 10. The details of the articulation device and the method of using the articulation device are described fully in my aforementioned U.S. Patent and will not be further described nor explained here.

A downwardly extending flange 24 can be provided, as shown in FIG. 2 around the perimeter of the tray along the opposite sides and front end of the tray 10. The flange 24 simply adds dimensional stability to the tray 10, and is not absolutely necessary.

The invention claimed is:

1. A dental model tray for use in forming a dental model from casting material poured on said tray and wherein the resulting, hardened, dental model is retained on the tray with upstanding projections that extend into the hardened, dental model, said dental model tray comprising a substantially planar base wall that forms the floor upon which dental casting material is poured in forming a dental model, said base wall being formed from a polymeric material;

a plurality of spaced apart, elongate projections extending upwardly from an upper face of said base wall so that an elongate central axis of each of said projections is substantially perpendicular to the upper face of said base wall, said projections being formed of polymeric material and integrally connected to said base wall;

said projections being arranged in two and only two, substantially parallel rows, with said projections in a first row of said two rows being offset from corresponding projections in a second row of said two rows so that any two adjacent projections in said first row and a mutually corresponding projection in said second row are spaced from each other in a triangular configuration;

each of said projections has an upstanding sidewall that tapers inwardly from said base end of each of said projections toward said central axis of each of said projections so that the sidewall of each of said projections makes an angle of between about 82 to 87 degrees with said upper face of said base wall;

each of said projections has a cross-sectional thickness at its said base end of between about 3 millimeters and 7 millimeters; and said projections are spaced apart so that the distance between said base ends of adjacent projections is between 0 millimeter and about 5 millimeters.

2. The dental model tray in accordance with claim 1 wherein said sidewalls of said projections make an angle of between about 83 degrees and 87 degrees with said upper face of said base wall.

3. The dental model tray in accordance with claim 2 wherein said sidewalls of said projections make an angle of about 85 degrees with said upper surface of said base wall.

4. The dental model tray in accordance with claim 1 wherein top ends of said projections have rounded edges joining said top ends with said sidewalls of said projections so that the said projections have surfaces that are smooth and have no sharp edges.

* * * * *